(12) United States Patent
Kamiar et al.

(10) Patent No.: US 8,109,890 B2
(45) Date of Patent: Feb. 7, 2012

(54) BODY MOVEMENT MONITORING DEVICE

(75) Inventors: Aminian Kamiar, Bussigny (CH); Najafi Bijan, Lausanne (CH); Gramiger Jean, Lausanne (CH); Morel Pascal, Echallens (CH)

(73) Assignee: Ecole Polytechnique Federale de Lausanne-Service des Relations Industrielles, Lausanne (CH)

( * ) Notice: Subject to any disclaimer, the term of this patent is extended or adjusted under 35 U.S.C. 154(b) by 706 days.

(21) Appl. No.: 10/502,850

(22) PCT Filed: Feb. 6, 2003

(86) PCT No.: PCT/CH03/00091
§ 371 (c)(1),
(2), (4) Date: Sep. 10, 2004

(87) PCT Pub. No.: WO03/065891
PCT Pub. Date: Aug. 14, 2003

(65) Prior Publication Data
US 2005/0010139 A1  Jan. 13, 2005

(30) Foreign Application Priority Data

Feb. 7, 2002 (WO) ........................ PCT/CH02/00075

(51) Int. Cl.
*A61B 5/117* (2006.01)
*A61B 5/103* (2006.01)
(52) U.S. Cl. .................................................. 600/595
(58) Field of Classification Search .......... 600/587, 600/595; 73/490, 865.4, 510, 504.12, 504.13; 702/160
See application file for complete search history.

(56) References Cited

U.S. PATENT DOCUMENTS

| | | | | |
|---|---|---|---|---|
| 2,290,387 | A * | 7/1942 | Schwartz | 600/595 |
| 4,616,320 | A * | 10/1986 | Kerr et al. | 702/14 |
| 5,656,777 | A * | 8/1997 | Petri et al. | 73/504.12 |
| 5,791,351 | A * | 8/1998 | Curchod | 600/595 |
| 5,941,837 | A * | 8/1999 | Amano et al. | 600/595 |
| 5,955,667 | A * | 9/1999 | Fyfe | 73/490 |
| 5,957,870 | A * | 9/1999 | Yamato et al. | 600/592 |
| 6,010,465 | A * | 1/2000 | Nashner | 600/595 |
| 6,135,951 | A * | 10/2000 | Richardson et al. | 600/300 |
| 6,524,239 | B1 * | 2/2003 | Reed et al. | 600/300 |
| 6,537,076 | B2 * | 3/2003 | McNitt et al. | 434/252 |
| 6,730,047 | B2 * | 5/2004 | Socci et al. | 600/595 |
| 6,984,208 | B2 * | 1/2006 | Zheng | 600/438 |

(Continued)

FOREIGN PATENT DOCUMENTS

EP  1 195 139  4/2002

(Continued)

OTHER PUBLICATIONS

Lortz, John and Leavitt, Susan. Smart Computing Learning Series: Wireless Computing "What is Bluetooth?". 2002. Sandhills Publishing Company. vol. 8 Issue 5, 72-73.*

(Continued)

*Primary Examiner* — Brian Szmal
(74) *Attorney, Agent, or Firm* — Nixon & Vanderhye P.C.

(57) ABSTRACT

An autonomous sensing unit and system that includes a set of sensors, a conditioning means for deriving information from the sensors, display means for displaying the information to an operator, and a means for recording the kinematic parameters of a body segment, and a method for using the system.

5 Claims, 8 Drawing Sheets

U.S. PATENT DOCUMENTS

| | | | |
|---|---|---|---|
| 2003/0009308 A1* | 1/2003 | Kirtley | 702/141 |
| 2004/0015103 A1* | 1/2004 | Aminian et al. | 600/595 |
| 2004/0133081 A1* | 7/2004 | Teller et al. | 600/300 |
| 2004/0167420 A1* | 8/2004 | Song et al. | 600/547 |
| 2004/0225236 A1* | 11/2004 | Wheeler et al. | 600/595 |
| 2005/0192516 A1* | 9/2005 | Takiguchi et al. | 600/595 |

FOREIGN PATENT DOCUMENTS

| | | | |
|---|---|---|---|
| WO | WO 01/08417 | * | 2/2001 |
| WO | WO 01/10508 | | 2/2001 |
| WO | WO 02091923 A1 | * | 11/2002 |

OTHER PUBLICATIONS

Aminian et al. Temporal feature estimation during walking using miniature accelerometers: an analysis of gait improvement after hip arthroplasty, medical and biological engineering and computing, Nov. 1999, Peter Peregrinus LTD, vol. 37 No. 6, pp. 686-691.*

Aminian, K., Rezakhanlou, K., DeAndres, E., Fritsh, C., Leyvraz, P.F., and Robert, P. Temporal feature estimation during walking using miniture accelerometers: an analysis of gait improvement after hip arthroplasty, 1999, Medical & Biological Engineering & Computing, vol. 37, pp. 686-691.*

Bruderlin et al, Goal-Directed, Dynamic Animation of Human Walking, Computer Graphics, vol. 23, No. 3, Jul. 1989, pp. 233-242.*

Abu-Faraj, Z.O., et al, A Holter-Type Microprossor-Based Rehabilitation Instrument for Acquisition and Storage of Plantar Pressure Data in Children with Cerebral Palsy, *Journal of Rehabilitation Research and Development*, 34, 187-194.

Aminian, K., et al, Incline, speed, and distance assessment during unconstrained walking, *Medicine and Science in Sports and Exercise*, 27, 226-34.

Aminian, K., et al, Temporal feature estimation during walking using miniature accelerometers: an analysis of gait improvement after hip arthroplasty, *Medical & Biological Engineering & Computing*, 1999, vol. 37, pp. 686-691.

Czerniecki, J.M., et al, Gait analysis in the amputee: Has it helped the amputee or contributed to the development of improved prosthetic components?, *Gait & Posture*, 4 (1996) 258-268.

Evans, A. L., et al, Recording Accelerations in Body Movements, *Med. & Biol. Eng. & Comput.*, 1991, 29, 102-104.

Ferrigno, G., et al, ELITE: A Digital Dedicated Hardware System for Movement Analysis Via Real-Time TV Signal Processing, *IEEE Transactions on Biomedical Engineering*, vol. BME-32, No. 11, Nov. 1985, pp. 943-950.

Hirokawa, S., et al, Gait Analysis Using a Measuring Walkway for Temporal and Distance Factors, *Med. & Biol. Eng. & Comput.*, 1987, 25, 577-582.

Hreljac, A., et al, Algorithms to Determine Event Timing During Normal Walking Using Kinematic Data, *Journal of Biomechanics*, 33 (2000) 783-786.

Ismail, A.R., et al, Discrete Wavelet Transform: A Tool in Smoothing Kinematic Data, *Journal of Biomechanics*, 32 (1999) 317-321.

Makai, B.E., Gait Changes in Older Adults: Predictors of Falls or Indicators of Fear?, *Journal of the American Geriatrics Society*, 45:313-320, 1997.

Mallat, S.G., A Theory for Multiresolution Signal Decomposition: The Wavelet Representation, *IEEE Transactions on Pattern Analysis and Machine Intelligence*, vol. 11, No. 7, Jul. 1989, pp. 674-693.

Miyazaki, S., Long-Term Unrestrained Measurement of Stride Length and Walking Velocity Utilizing a Piezoelectric Gyroscope, *IEEE Transactions on Biomedical Engineering*, vol. 44, No. 8, Aug. 1997.

Najafi, B., et al, Body Postures and Walking Period Estimation Using a Kinematic Sensor: Application for Long Term Monitoring of Physical Activity in Elderly Subjects, ESMAC-2001, *Gait & Posture*, 14, 119-120.

Najafi, B., et al, Fall Risk Assessment in Elderly PersonUsing Miniature Gyroscope: Relation between gait and risk of Falling, in: Duysens J, Smits-Engelsman B C M and Kingma H, (Eds.), Control of posture and gain. Symposium of the International Society for Postural- and Gait Research (ISPG 2001), Maastricht, pp. 136-139.

Nene, A., et al, Assessment of rectus femoris function during initial swing phase, *Gait and Posture*, 9, 1-9 (1999).

Pappas, I.P., et al, A Novel Gait Phase Detection System, *In Processing of Automated '99, 2. Workshop, Automatisierungstechnische Verfahren der Medizin*, U Darmstadt, 25, Feb. 26, 1999, pp. 69-70.

Rose, Jessica, et al, Human Walking, Second Edition, Baltimore. Williams & Wilkins, pp. 62-72.

Sparks, D.R., et al, Angular rate sensor and accelerometer combined on the same micromachined CMOS chip. In: *Microsystem Technologies 4*, Springer-Verlag, (1998) pp. 139-142.

Stanhope, S.J., et al, Kinematic-based technique for event time determination during gait, *Medical & Biological Engineering & Computing*, Jul. 28, 1990, pp. 355-360.

Aminian et al, "Temporal feature estimation during walking using miniature accelerometers: an analysis of gait improvement after hip arthroplasty", Medical & Biological Engineering and Computing, Peter Peregrinus Ltd., Stevenage, GB, vol. 37, No. 6, Nov. 1999, pp. 686-691.

Tong et al, "A practical gait analysis system using gyroscopes", Medical Engineering and Physics, vol. 21, 1999. pp. 87-94.

* cited by examiner (a)     (b)

BODY MOVEMENT MONITORING DEVICE

This application is the US national phase of international application PCT/CH03/00091 filed 6 Feb. 2003 which designated the U.S. and claims benefit of PCT/CH02/00075, dated 7 Feb. 2002, the entire content of which is hereby incorporated by reference.

The present invention relates to a device for measuring body movement and more precisely for measuring gait parameters.

The invention also relates to a method for using said device.

Walking is one of the most common human physical activities. Evaluation of time and distance parameters during walking is helpful in assessing abnormal gait, to quantify improvement resulting from interventions, or to predict subsequent events such as falls. This evaluation is useful in several clinical situations such as: functional performance assessment after treatment or surgery such as hip and knee arthroplasty (Wall et al., 1981), refining proper alignment and fit of external prosthesis or orthesis (Czerniecki and Gitter, 1996), fall risk assessment in elderly persons (Maki, 1997), or selecting the appropriate assistive device.

A gait laboratory based on camera, walkway with implanted sensors (Hirokawa and Matsumara, 1987) or forceplates, and electromyography allows a complete gait analysis but require a dedicated laboratory. Although these techniques have been widely used for research purposes, their sophistication, time required for setting up the instrumentation and analyze the data, as well as cost, have hindered their use in clinical practice. In addition, these techniques require the subjects to walk in a pre-defined specific path, and assume that data measured from only a few steps are representative of usual gait performance. To avoid these limitations, ambulatory recording systems carried by the subject and allowing outdoor measurement have been developed, using new technology, such as a powerful microcontroler, miniature sensors, high capacity memory and small batteries.

Ambulatory systems using foot switches or pressure sensors attached to the sole are used to monitor temporal parameters (Zhu et al., 1991; Abu-Faraj et al., 1997). These techniques provide satisfactory results for normal walking, but sensor attachment proves difficult when assessing subjects with abnormal gait. Even when correctly done, several problems, such as shuffling gait, mechanical failure, or patient acceptance limit their applicability. Another system using insole with a matrix of multitude pressure sensors has a high reliability to evaluate the time of each phase of the gait cycle. Although this system provides additional information on foot pressure distribution during gait, it cannot be used for a long period of measurement, and sensors do not provide information during the swing phase.

Recently, technical progress has made possible the realization of miniature kinematic sensors such as accelerometers and angular rate sensors with integrated conditioning and calibrating module (Sparks et al., 1998). In addition, due to their very low consumption, these sensors can be battery powered and are promising tools for long term ambulatory monitoring. The possibility of detecting simple parameters such as steps and cycle time from trunk or heel acceleration has already been demonstrated using miniature accelerometers (Evans et al., 1991; Aminian et al., 1995). More recently the efficiency of accelerometers to detect temporal features of walking has been shown (Aminian et al., 1999). However, the acceleration signal is often biased by the gravitational acceleration and depends on the attachment site along the segment (e.g. limb). Fyfe et al. (2000) have proposed a motion analysis system, which measured the stride length and velocity of the foot. However, this system do not provided information related to the lower limbs rotation and temporal parameters. Since the actual nature of walking consists of lower limb rotation around joint articulation, the use of miniature angular rate sensors (gyroscopes) has proven to be an alternative technique for gait analysis (Tong and Granat, 1999, Nene et al., 1999). However, no clear correspondence has been established between gait events and the patterns of angular velocity. This is probably because gait events (e.g. heel strike and toe-off) are transitory signals that cannot be properly enhanced by traditional signal processing.

1 SUMMARY OF THE INVENTION

One of the objectives of the present invention is to avoid the previous cited problems.

It relates to a body movement monitoring unit as defined in claim 1 and to a corresponding method as defined in claim 7.

In a preferred embodiment wavelet transform is used to overcome the previous discussed problems.

What follows is a description of an ambulatory system according to the invention which is based on autonomous sensing units (ASU) for estimation of spatio-temporal parameters during long periods of walking. The method according to the invention is based on wavelet transform to compute the values of gait parameters from the angular velocity of lower limbs. The accuracy of measurements was assessed, using as a criterion standard the information provided by standard such as foot pressure sensors, forceplate and cameras. In order to estimate the accuracy of the method on a broad range of performance for each gait parameter, data were gathered from young (group A) elderly (groupe B) and subjects. The usefulness and the reliability of the proposed methods and device have been shown by performing gait analysis in three populations: patients with coxarthrosis (group C), patients with total hip arthroplasty (group D) and subjects age matched to the other two groups (group E).

2 METHODS

An autonomous sensing unit (ASU) was designed including a set of sensors 10, conditioning circuit 20 (powering, amplifying and filtering), analog to digital converter, display 30, high capacity digital memory 40 (64 Mbytes or more), rechargeable battery 70, and a microcontroller which controls the above components. The ASU was embedded in a small case and allowed saving signals detected by the sensors for a long period (FIG. 1). This configuration avoids the use of cable between sensors and a dattalogger and presents an easy way for attachment and comfort of the subject. The device allows also recording acceleration, angular rate in different axis of movement and also detecting temperature in order to compensate kinematic signal (acceleration and angular rate) for temperature variation. Lower limbs movement during walking was measured using miniature angular rate sensors: gyroscopes. The gyroscope consists of a vibrating element coupled to a sensing element, acting as a Coriolis sensor. Coriolis effect is an apparent force that arises in a rotating reference frame and is proportional to the angular rate of rotation. Currently, Coriolis effect is used in several miniature gyroscopes such as piezoelectric gyroscope (Murata, ENC-03J) or MEMS gyroscope (Analog device, ADXRS300). Because of their low current consumption, these sensors can be battery powered and are therefore appropriate for ambulatory monitoring.

Four ASUs including each at least one gyroscope were used. Using the conditioning electronic of the ASU, the signal from each gyroscope was amplified and low-pass filtered to remove the electronic noise of the gyroscope. A swiveling electromechanical system was designed to calibrate and characterize each sensor. Various angular velocities were applied to the gyroscope. An optical sensor measured the time corresponding to perform a rotation of 360° and allowed calibration of the gyroscope. The amplifier gain of each gyroscope was set to obtain a sensitivity of 4 mV/deg/s. The ASUs were attached with a rubber band to each shank and on each thigh. Each ASU measured the angular rate rotation parallel to the mediolateral axis (perpendicular to the sagittal plane). The signals were digitized at a sampling rate of 200 Hz and stored on the memory of ASU. In order to synchronize the signal detected by each ASU and be able later to compare their values, before the measurement, all ASU were connected to the station unit which allowed starting all ASUs at the same time. During the recording the ASUs were disconnected from the station and attached on lower limbs. At the end of the recording all ASUs were connected again to the station. The recording was stopped with the station unit. Afterward, the data saved on each ASU were transferred to a computer via the station unit and an USB port. The station unit has three major tasks: synchronizing all measurements, downloading recorded data to the computer and recharging the batteries of all ASU.

2.2 Validation with Footswitches

Footswitches have been used as criterion standard to detect the gait events and validate the gyroscope measuring method. The footswitches consisted of two pairs of force sensing resistors, FSR (Interlink, LU) placed under the right foot (FIG. 2): $FSR_{heel}$ beneath the heel (two sensors) and $FSR_{toe}$ beneath the big toe (two sensors). For each pair, the sensors were connected in series and the outputs were synchronized with those from the gyroscopes and recorded using a portable datalogger at a sampling rate of 200 Hz. During heelstrike and toe-off, $FSR_{heel}$ and $FSR_{toe}$ signals are subjected to abrupt changes. By thresholding the derivative of these two signals the exact time of heelstrike and toe-off was obtained.

2.3 Validation with Forceplate and Camera Based System

Gait Analysis was performed by means of a motion analyzer (ELITE System, BTS SrL, Milano, Italy) equipped with 4 video-cameras recording at 100 Hz (Ferrigno G., Pedotti 1985). One forceplate (Kistler 9661 A, 60 by 40 cm large) was embedded in the floor about one third down a 10 meters long walking pathway. Signals from the forceplate were collected at 500 Hz. The retroreflective markers were positioned on the lower limbs (fifth metatarsal head, lateral malleolus, lateral femoral epicondyle), on the pelvis (posterior iliac spines and lower edge of sacrum), and spine (posterior processes of seventh vertebra and point of maximum kyphosis). Joint kinematics was confined to only flexiontextension angles at the hip, knee, and ankle joints.

The spatio-temporal parameters were computed on the basis of the heelstrike and toe-off (respectively initial and terminal contacts) of each foot on the ground. The forceplate was used to detect the initial contact of one foot. This was defined when the ground reaction force achieved a threshold of 5% of body weight. The next contact of the foot on the ground occurred in a non-instrumented area of the floor. Contact was defined when a similar markers' configuration was achieved (same distance from the floor, same displacement) as in the contact detected by the forceplate. The contralateral side was analyzed by looking at the distance of the foot from the ground.

2.4 Validation with Treadmill

In order to evaluate the accuracy of stride length and velocity, the following measurements were carried out. During treadmill walking, the value of treadmill speed has been considered as the actual mean walking velocity. A preliminary experiment in which various treadmill speeds were compared to the speed of an odometer placed on the treadmill belt confirmed that the treadmill speed is accurate. During ground (or "non-treadmill") walking, the mean velocity was evaluated by considering the time needed to cover 20 m using a stopwatch. The actual mean stride length was calculated by multiplying the mean velocity by the gait cycle time obtained from footswitches.

2.5 Subjects

Measurement using gyroscopes and FSR were taken from group A (9 young subjects, 21±2 yrs) and group B (11 elderly, 79±8 yrs). Each young subject performed four trials including at least 20 gait cycles. The first three trials were performed on a treadmill at the preferred speed, under and over the preferred speed, respectively. The fourth trial was performed with a comfortable velocity over ground on a 30 m long walkway. The elderly performed only two trials on the walkway at their comfortable velocity. The study protocol was accepted by the institutional review board (Faculty of Medicine, University of Lausanne). Written informed consent was obtained from each subject.

Measurements using gyroscopes, forceplate and Elite camera system were taken from group C (11 patients with unilateral coxarthrosis, age: 60±9 yrs), group D (8 patients with unilateral total hip prosthesis, age: 69±4 yrs) and group E (9 healthy subjects, 63±4 yrs, weight: 63±9 kg). Each patient was asked to walk at a self-selected velocity down a walkway that included the forceplate. In order to reach good precision for the temporal parameters, each subject performed several trials (6 to 10 depending on patient condition, half with left foot touching the forceplate and half with right foot). At the end of the measurement, the exact time of toe-off and heel-strike extracted by both of the systems (gyroscopes and Elite/forceplate) were compared.

2.6 Wavelet Analysis: Gait Temporal Parameters Estimation

In order to compute the temporal parameters such as the duration of swing, single and double stances during a gait cycle, it is necessary and sufficient to determine for each leg the precise moments of heelstrike (when the foot first touches the floor) and toe-off (when it takes off) during that cycle. These events have distinctive signal features of shank angular velocity appearing as rather sharp negative peaks involving some medium and relative high frequencies (FIG. 3). Although the amplitude of these peaks vary according to various parameters such as subject's velocity or weight, or the presence of limping due to a painful articulation, they can always be localized as long as one knows where to look for it in time and frequency domains. To successfully achieve this task, we have decomposed the shank angular velocity into wavelet packages. Wavelet transformation is well adapted for gait events identification because it allows detection of a specified frequency at a specified time (e.g. toe-off and heel strike). In other words, toe-off and heel strikes events consist of combined features that can be well located in the time and frequency range. The methods of analysis need to be versatile enough to handle gait events that can be at opposite extremes in terms of their time-frequency location. Moreover, wavelets transformation allows the use of a suitable wavelet function (Coiflet wavelet), which is more similar to the pattern of heel strike and toe-off.

A multi-resolution wavelet decomposition (Mallat, 1989) was used to enhance the toe-off and heel-strike event during walking. This technique consists in splitting a signal into high-scale (low-frequency components) called approximation and low-scale (high-frequency components) called detail. The decomposition is iterated, with successive approximations (or details) being decomposed in turn, so the original signal is broken down into many lower-resolution components. At each decomposition scale the number of samples in the time domain is decreased by throwing away every second sample (down sampling with a factor of '2'). By considering the original signal s(n) (shank angular velocity), the approximation of the signal at scale j=0 is $A_{2^0}s$ which corresponds to the original signal s(n). At each new decomposition the approximation and detail decrease in resolution since at each scale 2 samples will be replaced by one. At scale j the $A_{2^j}s$ represents approximation of s(n) with a resolution of one sample for every $2^j$ samples of the original signal. We have:

$$s = A_{2^1}s + D_{2^1}s = A_{2^2}s + D_{2^2}s + D_{2^1}s = \ldots = A_{2^j}s + D_{2^j}s + D_{2^{j-1}}s \ldots + D_{2^1}s \quad (1)$$

Thus:

$$A_{2^j}s = A_{2^{j+1}}s + D_{2^{j+1}}s \quad (2)$$

By using a suitable low-pass filter h, and a high-pass filter g, the approximate signal $A_{2^{j+1}}s$ and detail signal $D_{2^{j+1}}s$ can be further written as following:

$$A_{2^{j+1}}s = \sum_{k=-\infty}^{+\infty} h(2n-k) A_{2^j}s \quad (3)$$

$$D_{2^{j+1}}s = \sum_{k=-\infty}^{+\infty} g(2n-k) A_{2^j}s \quad (4)$$

Furthermore the signal can be reconstructed from approximate and detail signal using the following transform:

$$A_{2^j}s = 2 \sum_{k=-\infty}^{+\infty} \tilde{h}(n-2k) A_{2^{j+1}}s + 2 \sum_{k=-\infty}^{+\infty} \tilde{g}(n-2k) D_{2^{j+1}}s \quad (5)$$

Where, $$\tilde{h}(n) = h(-n), \quad (6)$$

$$\tilde{g}(n) = g(-n) \quad (7)$$

The coefficients of h and g filter are associated with the shape of wavelet considered for the analysis. In this study, a decomposition into 10 scales with the Coiflet wavelet of order 5 has been used.

The flowchart for the estimation of toe-off and heel-strikes are shown in FIG. 4. For clarity, let us consider only one shank. It is obvious that the algorithm will be applied in the same way for both shanks. First an approximation of s(n) corresponding to the $$s_a = \sum_{j=1}^{9} D_{2^j}s$$

was obtained. With this approximation the original signal was only considered in the range of 0.14 to 36 Hz. Drift and high frequency movement artifacts were canceled in this way. Then two new approximations were obtained. The first one enhanced the heel strike component ($A_{2^1}s_a - A_{2^0}s_a$) and the second one enhanced the toe-off component ($A_{2^3}s_a - A_{2^0}s_a$).

For each of these approximations, the time corresponding to the global maximum values of the signal (ms) were detected. These values corresponded roughly to the time of midswing during a gait cycle (see FIG. 5), however their exact significance is not of interest to us. They will only be used as reference to select the intervals in which negative peaks reminiscent of heelstrikes and toe-offs are to be found. So we next looked for local minima inside intervals [ms+0.25 s, ms+2 s] and [ms−2s, ms−0.05 s], assuming that a gait cycle is always less than 2s. The result was two different series of samples hs (heelstrikes) and to (toe-offs). The toe-off detection was refined by finding the local minima inside of the original signal s in the intervals [to, to +0.075s]. Finally, at each cycle, the actual heelstrike and toe-off must be so that their difference is considered reasonable for walking. Thus, for each hs(k) only the nearest to(l) verifying the condition 0.1s<hs(k)−to(l)<2.5 s was saved. If no to(l) met this condition, h(k) was deleted and the next heelstrike was considered. Once we are in possession of $hs_L$ (left heel strike), $to_L$ (left toe-off), $hs_R$ (right heel strike) and $to_R$ (right toe-off), every temporal parameter of a gait cycle can be easily computed as percentage of gait cycle. These parameters are:

Duration of each gait cycle (measured at right or left leg)

$$RGCT(k) = to_R(k+1) - to_R(k) \text{ or } LGCT(k) = to_L(k+1) - to_L(k), 1 \leq k \leq N, \quad (8)$$

N: number of gait cycles

Left stance (time between left heel strike and left toe-off)

$$LS(k) = to_L(k) - hs_L(k)) \quad (9)$$

Right stance (time between right heel strike and right toe-off)

$$RS(k) = to_R(k) - hs_R(k) \quad (10)$$

Initial double support (time between right heel strike and left toe-off), known also as left double thrust support time (Wall et al., 1981))

$$IDS(k) = to_L(k) - hs_R(k) \quad (11)$$

Terminal double support (time between left heel strike and right toe-off), known also as right double thrust support time (Wall et al., 1981)

$$TDS(k) = to_R(k+1) - hs_L(k) \quad (12)$$

Double support $$DS(k) = IDS(k) + TDS(k) \quad (13)$$

In order to reach a good precision for the temporal parameters, at least 20 gait cycles have been considered for analysis (N>20). For each trial, the value of temporal parameters was averaged over the N cycles. Statistical analysis is then performed to find the significance and accuracy of the parameters obtained by gyroscopes in comparison with the FSR based system. The root mean square error (RMSE) was used to analyze the average difference between estimated data by gyroscope and actual data obtained by FSR.

$$RMSE = \sqrt{\frac{\sum_{\text{number of samples}} (\text{estimated} - \text{actual})^2}{\text{number of samples}}} \quad (14)$$

2.7 Temporal Parameters Estimation Using IIR Filtering

The wavelet filter described above is a kind of bandpass filter. The low-pass part was used to "smooth" the signal a bit to increase the precision in locating the peaks and a high-pass part to get rid of drift.

Another technique to cancel the drift would be the Infinite Impulse Response (IIR) filter. The IIR filter used has the following transfer function:

$$y(z) = \frac{1 - z^{-1}}{1 - \alpha z^{-1}} \quad (15)$$

The value of α used during mentioned statistical study was 0.995. Using this filter the cut-off frequency of the filter will be 0.25 Hz. To obtain precisely zero-phase distortion, the filter was applied on the input data twice. After filtering in the forward direction, the filtered sequence was reversed and run back through the filter. To detect heelstrike, the mentioned IIR filter was used and to detect toe-off, after applying the same IIR filter, a Finite Impulse Response (FIR) low-pass filter with pass-band attenuation of less than 0.5 dB and a cut-off frequency of 30 Hz was used. To have zero-phase distortion the above forward and reverse filtering was used. This method of detection of toe-off and heelstrike was validated with 259 gait cycles recorded by both gyroscopes and force-plate. This filtering has the advantage to speed-up the calculation time.

2.8 Gait Model: Spatial Parameters Estimation

We propose a double segment gait model involving both shank and thigh. In this model, the swing phase is considered as a double pendulum model, while the stance phase is considered as an inverse double pendulum model. Consequently, knowledge of stance and swing phases obtained from the method described in 2.6 is necessary. FIG. 6(a) illustrates the rotation of the shanks and thighs during a complete gait cycle. The distance $d_1 + d_2$ corresponds to the part of stride length performing by the swing of right shank and right thigh. In addition, during this right swing phase, the body has moved forward by the distance $d_3$ involved by the rotation of left shank and left thigh throughout the contralateral stance phase. Stride length (SL) can then be measured as follows:

$$SL = d_1 + d_2 + d_3 \quad (16)$$

By considering α and β to be the angular rotation of the right thigh and right shank respectively, one can calculate the distance $d = d_1 + d_2$ from the trigonometric relations (FIG. 6.b).

During the swing phase we have for each gait cycle k:

$$d(k) = d_1(k) + d_2(k) = \sqrt{(l_2 + M_1(k))^2 + (l_2 + M_2(k))^2 - (l_2 + M_1(k)) \cdot (l_2 + M_2(k)) \cdot \cos\beta(k)} \quad (17)$$

where:
$l_1$: thigh length
$l_2$: shank length $$M_1(k) = \frac{\sin\varphi(k)}{\sin\beta(k)} d'(k) \quad (18)$$

$$M_2(k) = \frac{\sin\gamma(k)}{\sin\beta(k)} d'(k) \quad (19)$$

with: $\gamma(k) = \frac{\pi - \alpha(k)}{2}$ and $\varphi(k) = \frac{\pi - 2\beta(k) + \alpha(k)}{2}$ and $d'(k) = l_1 \sqrt{2(1 - \cos\alpha(k))}$ The angles α and β were estimated by integration of the angular rate rotations of the right thigh ($t_R$) and right shank ($s_R$) as follow:

$$\alpha(k) = \int_{to_R(k)}^{hs_R(k)} t_R(t) \cdot dt \quad (21)$$

$$\beta(k) = \int_{to_R(k)}^{hs_R(k)} s_R(t) \cdot dt$$

During the stance phase we have:

$$d(k) = d_3(k) = \sqrt{(l_1 + M_2(k))^2 + (l_1 + M_1(k))^2 - (l_1 + M_2(k)) \cdot (l_1 + M_1(k)) \cdot \cos\alpha(k)} \quad (22)$$

where:

$$M_1(k) = \frac{\sin\varphi(k)}{\sin\beta(k)} d'(k) \quad (23)$$

$$M_2(k) = \frac{\sin\gamma(k)}{\sin\beta(k)} d'(k) \quad (24)$$

with: $\gamma(k) = \frac{\pi - \beta(k)}{2}$ and $\varphi(k) = \frac{\pi - 2\alpha(k) + \beta(k)}{2}$ (25)

and $d'(k) = l_2(k) \sqrt{2(1 - \cos\beta(k))}$ and:

$$\alpha(k) = \int_{hs_L(k)}^{to_L(k)} t_R(t) \cdot dt \quad \beta(k) = \int_{hs_L(k)}^{to_L(k)} s_R(t) \cdot dt \quad (26)$$

For each gait cycle k, the stride length (SL) and stride velocity (SV) were obtained as follow:

$$SL(k) = d_1(k) + d_2(k) + d_3(k) \quad (27)$$

$$SV(k) = \frac{SL(k)}{RGCT(k)} \quad (28)$$

where RGCT(k) was obtained from (8).

If necessary, we can use only three gyroscopes instead of four, by assuming the same length for left and right steps, one can consider that the rotation during left stance phase is equal to rotation during right stance phase. In this case (26) change to:

$$\alpha(k) = \int_{hs_R(k)}^{to_R(k)} t_R(t) \cdot dt \quad \beta(k) = \int_{hs_R(k)}^{to_R(k)} s_R(t) \cdot dt \quad (29)$$

2.9 Comparison with References Systems

Toe-off and heelstrike events were estimated using FSR (footswitches) in group A and B and using forceplate and Elite camera based systems in groups C, D and E. At the end of the measurement, the exact time of these events were compared to those estimated based gyroscopes.

In order to evaluate the accuracy of stride length and velocity given by (27) and (28), the following measurements were carried out. For group A treadmill will used, the value of treadmill speed has been considered as the actual mean walking velocity ($V_a$). For group B only overground walking was performed. The mean velocity was evaluated by considering the time needed to cover 20 m using a stopwatch. The actual mean stride length ($L_a$) was calculated as:

$$L_a = V_a \cdot GCT_a \quad (30)$$

where $GCT_a$ is the mean gait cycle time obtained from foot-switches. The accuracy of stride length and velocity was evaluated by comparing $L_a$ and $V_a$ with the mean of SL and SV($SL_m$ and $SV_m$) over 20 m.

In group C, D and E stride-length and velocity ($SL_a$ and $SV_a$) were obtained for each cycle based on Elite and force-plate systems as explained earlier and compare to our estimated values ($SL_m$ and $SV_m$).

3 RESULTS

3.1 Temporal Parameters

The correspondence between temporal events detected by FSR and the gyroscope pattern is shown in FIG. 5 for five consecutive gait cycles. Using the algorithm of FIG. 4, left and right heel strikes (respectively toe-off) were detected from shank gyroscopes (FIG. 7). Then based on relation (8) to (13), the mean value (over the N cycles) of left and right gait cycle time ($LGCT_m$, $RGCT_m$), left and right stance ($LS_m$ and $RS_m$), initial and terminal double stance ($IDS_m$, $TDS_m$, $DS_m$) were computed for each trial on treadmill and ground. Simultaneously, the periods of the actual gait cycle ($GCT_a$) and right stance ($RS_a$) were detected from $FSR_{heel}$ and $FSR_{toe}$.

FIG. 8 compares stance period ($RS_m$ and $RS_a$) and gait cycle times values ($RGCT_m$ and $GCT_a$) obtained from the gyroscopes to those of FSR from a trial performed by the group A (young subjects: treadmill and ground) and group B (elderly during overground walking). A good agreement (r>0.99) was found. The difference between $RS_m$ and $RS_a$ was not significant (N=58, p>0.80) with a mean standard error RMSE=23 ms. No significant change was observed between $RGCT_m$ and $GCT_a$ (N=58, p>0.97). The RMSE between $RGCT_m$ and $GCT_a$ was 8 ms (0.5%). The 95% confidence interval for the difference between heelstrike detection by FSR and gyroscope was [7 ms, 13 ms]. Heelstrike detection based on the gyroscopes occurred later (10 ms in average) than FSR (underestimation). The 95% confidence interval for the difference between toe-off detection by FSR and the gyroscopes was [−5 ms, 4 ms]. Therefore there was no significant difference in toe-off detection. The RMSE between $LGCT_m$ and RGCT, was 15 ms (r>0.99, 1.3%), which shows the validity of the method in providing the same time for both left and right gait cycles.

The mean values of right and left stance ($RS_m$ and $LS_m$) as well as double supports ($TDS_m$, $IDS_m$, $DS_m$) estimated by the gyroscopes are shown in table 1. In general, higher values are observed for elderly subjects (group B).

TABLE 1

The averaged values of right stance ($RS_m$), left stance ($LS_m$), initial double stance ($IDS_m$), terminal double stance ($TDS_m$) and double stance ($DS_m$) in the percentage of gait cycle obtained for young (group A) and elderly subjects (group B).

| Subjects | $RS_m$, % | $LS_m$, % | $IDS_m$, % | $TDS_m$, % | $DS_m$, % |
|---|---|---|---|---|---|
| Group A(Young) | 61 ± 2 | 62 ± 2 | 12 ± 2 | 12 ± 2 | 23 ± 3 |
| Group B(Elderly) | 64 ± 3 | 65 ± 2 | 14 ± 3 | 15 ± 2 | 29 ± 4 |

A total of 106, 80 and 83 gait cycles were obtained from groups C, D and E, respectively. A good correspondence was observed between gyroscopes and the Elite system. By considering all the gait cycles (N=269), a systematic difference of −14 ms was observed between the actual initial contact (from the forceplate) and the corresponding value detected by gyroscopes. This difference reached 4 ms for terminal contact. Gyroscopes detect slightly later the heelstrike of the foot, while toe-off detection based on gyroscopes occurred a little earlier than with the forceplate. The same trends were observed within each group C, D and E. Assuming this difference as a systematic error, the values of toe-off and heel-strike were corrected by considering these differences. Students t-tests applied on temporal parameters showed no significant difference (p>0.99) between the actual values of gait cycle time and stance period, as compared to those estimated by gyroscopes. Table 2 illustrates for group C, D and E, the RMSE and the overall coefficient of correlation versus the actual values. The error ranged between 2.7% and 4.6% (3.7% when considering all subjects).

3.2 Spatial Parameters

In group A and B, for each trial the mean value of stride length and velocity ($SL_m$ and $SV_m$) were estimated by finding the average of stride length (SL) and stride velocity SV (relation 27 and 28-) over the 20 m of walking. FIG. 9 compares actual $L_a$ and $V_a$ to $SL_m$ and $SV_m$. No significant change was found between $L_a$ and $SL_m$ (N=56, p>0.52) and neither between $V_a$ and $SV_m$ (p>0.66). The coefficient of correlation is high in both cases (r>0.96). Actual velocity and stride length can be estimated from the measured values as follow:

$$V_a = 1.02 SV_m - 0.04 \quad (31)$$

$$L_a = 0.97 SL_m \quad (32)$$

The RMSE for velocity estimation is 0.06 m/s (6.7%) and that of stride length estimation is 0.07 m (7.2%).

Stride length and velocity had lower averaged values for the elderly (group B) compared to young subjects (group A).

In groups C, D and E, stride length and velocity, shows also a linear relationship between actual ($SV_a$, $SL_a$) and gyroscopes values ($SV_m$, $SL_m$). When including all subjects in these 3 groups, we obtained the following linear regression:

$$SV_a = 0.931 SV_m + 0.006 \quad (33)$$

$$SL_a = 1.172 SL_m - 0.214 \quad (34)$$

When considering each group C, D, E separately, the slope and intercept were also close to the value of equation 31 and 32. Based on these linear approximations, the values of $SV_m$ and $SL_m$ were modified to be closer to the actual values (replacing the measured value by its linear approximation). The coefficient of correlation (r) and RMSE for spatial parameters are shown in table 2. The error ranged between 4.8% and 7.5% (overall error of 7%). No significant difference were observed between the actual values and those obtained from gyroscopes(p>0.99).

FIG. 10 compares the ranges of thigh and shank rotation estimated from gyroscopes with the corresponding values of the Elite system. A very good agreement (r=0.97) between the two systems can be observed. The overall RMSE was less than 5 degrees (Table 2).

TABLE 2

Error (RMSE) for gait events (toe-off and heelstrike, gait cycle, stance time) and spatial parameters (stride length and velocity, range of thigh and shank rotation) obtained for groups C, D, E and by considering all subjects of these three groups (overall). The overall correlations (r) show the good agreement between our proposed method and reference system.

| Group | RMSE | | | | r |
|---|---|---|---|---|---|
| | C | D | E | Overall | |
| Initial contact | 16 ms | 9 ms | 11 ms | 13 ms | >0.99 |
| Terminal contact | 23 ms | 34 ms | 24 ms | 28 ms | >0.99 |

TABLE 2-continued

Error (RMSE) for gait events (toe-off and heelstrike, gait cycle, stance time) and spatial parameters (stride length and velocity, range of thigh and shank rotation) obtained for groups C, D, E and by considering all subjects of these three groups (overall). The overall correlations (r) show the good agreement between our proposed method and reference system.

| Group | RMSE | | | | |
|---|---|---|---|---|---|
| | C | D | E | Overall | r |
| Gait cycle | 38 ms | 52 ms | 30 ms | 38 ms | 0.93 |
| Stance | 25 ms | 33 ms | 28 ms | 28 ms | 0.92 |
| Stride velocity | 0.07 m/s | 0.06 m/s | 0.08 m/s | 0.07 m/s | 0.88 |
| Stride length | 0.08 m | 0.05 m | 0.08 m | 0.08 m | 0.82 |
| Thigh rotation range | 4 deg | 7 deg | 5 deg | 5 deg | 0.82 |
| Shank rotation range | 3 deg | 2 deg | 2 deg | 3 deg | 0.94 |

FIG. 11 shows typical results obtained during 2 minutes of treadmill walking where the velocity was fixed at 1.11 m/s (4 km/h). The subject was asked to walk at his normal pace, to decrease his pace then increase his pace. All parameters were obtained at each gait cycle from gyroscopes. As it is illustrated, the estimated velocity (SP) is almost constant (mean=1.14 m/s) with a coefficient of variation of 4%. The change of gait cycle (RGCT) provides a corresponding change of stride length (SL) in order to maintain the velocity constant. The corresponding coefficient of variation of SL and RGCT is 15%. During the same period there is no significant variation of left and right stance (coefficient of variation less than 3%) while the double support time (DS) has a coefficient of variation of 16%.

Toe-off and heelstrike detection based on IIR and FIR filtering are compared favorably with wavelet techniques. In 259 gait-cycles the measured signals of gyroscopes were analyzed twice, once using the wavelet based filter and once using an IIR+FIR filter method. Table 3 compares the obtained results by using forceplate as reference.

TABLE 3

Toe-off and heelstrike detection by using the two proposed method of filtering: Wavelet filtering and IIR + FIR. Mean and standard deviation are expressed for 259 gait cycles.

| | | Mean (ms) | Std (ms) |
|---|---|---|---|
| Wavelet | Toe-off | 4.6 | 29.2 |
| | Heel-strike | −13.3 | 14.0 |
| IIR + FIR | Toe-off | −2.9 | 28.0 |
| | Heel-strike | −13.6 | 13.2 |

4 DISCUSSION

We have proposed a new algorithm based on wavelet transformation to detect toe-off and heelstrike from shank angular velocity. A high correlation with actual gait events detected by standard reference systems (foot pressure sensors, forceplate and camera) was found. In addition, no significant error was observed for temporal events detection. The slight delays that can be observed between reference systems and gyroscopes are in the range of resolution of the used systems. In addition, the obtained values correspond to the established values for young and elderly populations which is around 60% for the duration of stance and 20% for the duration of double support (Rose et al., 1994, Maki, 1997). Few studies have been reported about temporal gait parameters' detection based on gyroscope. Pappas et al. (1999) used a gyroscope on the heel in conjunction with FSR to detect the precise time of heel-off. Tong and Granat (1999) used a gyroscope on the shank and thigh. They found that the pattern on the shank has two minima, one occurs at foot flat and the other occurs at toe off. This last result is consistent with ours. In contrast to their results, we found that the first peak after wavelet enhancement corresponds to heel strike and not foot flat. It must be noted that only 2 subjects were involved in their study and the sampling rate was 50 Hz. Toe-off and heelstrike detection were based on the choice of a threshold on the FSR signal. It is clear that the value of the threshold can modify the results. Moreover, only a few steps were considered for analysis which can not be considered as statistically significant.

The method presented in this study compares favorably with other methods used to identify gait events that require more complex instrumentation and a laboratory setting. Hreljac and Marshall (2000) used four motion analysis cameras (60 Hz), involving 12 trials of two healthy subjects and found an absolute average error of 4.7 ms and 5.6 ms for heelstrike and toe-off, respectively, considering information from a forceplate as the "gold standard". Stanhope et al. (1990) using a 50 Hz camera collection system, reported an error greater than 20 ms in over 20% of the cases. Using accelerometers on the thigh and considering FSR as reference, Aminian et al. (1999) found the 95% confidence interval of stance period equal to [−20 ms, 20 ms]. In the present study, which involve young and elderly subjects the error of toe-off and heelstrike detection is less that 5 ms (95%), with a systematic delay for heelstrike time of 10 ms.

Gait events can also be explained by looking at the particular pattern of the shank and thigh angular velocities (FIG. 5). Shank angular velocity (signal $s_R$) is a bipolar signal. Considering as positive the counter-clockwise rotation, one can observe that during the swing period $s_R$ is rather positive while in stance phase $s_R$ is almost negative. Just prior to heelstrike, $s_R$ becomes negative. At heelstrike, there is a flexion (Vaughan et al., 1992) of the knee shown by a negative $s_R$ and positive $t_R$. The time of heelstrike is also characterized by a change of slope sign of $s_R$. This is expected since before heelstrike, the shank decelerates (negative slope) to stop and after heelstrike there is an acceleration (positive slope) due to rotation around the ankle. After heelstrike, there is a clockwise rotation of the shank around the ankle involving a negative $s_R$. In mid-stance, the knee becomes straight leading to a slight angular velocity, which could become positive. Then the shank continues its clockwise rotation around the ankle and accelerates its rotation at the toe-off (positive slope of $s_R$). The rotation is still clockwise ($s_R$ negative) at the beginning of the swing phase until the knee reaches its maximum flexion ($t_R$ is positive and $s_R$ negative), then the knee comes into extension ($s_R$ positive and $t_R$ positive) moving the shank from backward to forward. In this way, shank and thigh angular velocities also give remarkable insight into the recognition of the periods of knee flexion and extension during gait cycle.

In order to measure spatial parameters such as stride length, we have used the change of lower limb angles. Miyazaki (1997) has shown that for the estimation of the stride length from the integral of angular velocity, the relative change of angular rotation is sufficient and therefore there is no need of initial angular position. However this method consider thigh and shank as a unique segment and the error reached 15%. We propose a double segment gait model involving both shank and thigh, which consider a double pendulum model during the swing phase and the inverse double pendulum model during the stance phase. The identification of swing and stance phases was therefore necessary, and was determined by toe-off and heelstrike estimation. The estimation error for velocity and stride length is around 7%. This error is principally due to the inaccuracy of the gyroscopes which induce some error on a and 0 in (20) and (25). This error could increase if the period of integration increases considerably (very slow speed). In this case a new calibration of (29) and (30) is necessary. Other factors such as the difficulty to measure the exact shank and thigh length, the misalignment of the gyroscope axis regarding the mediolateral axis and the error due to gait phase detection are also to be considered. The low values of the intercept (close to 0) and the slope close to 1 in (29) and (30) confirm the appropriateness of the proposed gait model.

There are many advantages to use gyroscopes instead of other kinematic sensors such as accelerometers. First, unlike the accelerometer, the gyroscope can be attached to anywhere of any body segment as long as its axis is parallel to the mediolateral axis: the angular rotation is still the same along this segment. Tong and Granat (1999) have shown that the signals from different gyroscopes at different attachment site are almost identical. Second, the angular rate signal is less noisy than acceleration since acceleration is the derivative of velocity and involves higher frequency components. Third, accelerometry provides essentially temporal gait parameters, using singular peak enhancement. In contrast, rotation angles can be estimated from angular velocity by simple integration, and provides spatial gait parameters in addition to temporal parameters. Recently, the possibility to estimate knee angle (Williamson et al, 2001) and trunk tilt (Najafi et al, 2001$^a$) has also been shown. Finally, there is no influence of gravity acceleration on the measured signal. Gyroscopes however, do have some weaknesses. First, gyroscope is more delicate to use than accelerometer and can be more sensitive to temperature. In addition, powerful signal processing and filtering are necessary to cancel drift and artefact in the signal. Nevertheless, this filtering was done in this study by using wavelet transformation. The use of wavelet was particularly important to ensure a good time resolution in finding gait events such as toe-off and heelstrike.

Overall, the autonomous measuring devices (ASU) are light (each 80 gr), portable, wireless, low cost and involves no discomfort for the patient who carries it for a long period of time. The ASU is battery powered with a lifetime of 20 hours. It can collect data up to 64 Mbytes corresponding to a period of 42 hours (at 200 Hz sampling rate). The number of sensor to be used depends on application. Two gyroscopes can be used on one side (e.g. right shank and right thigh) where the estimation all temporal parameters is not desired. By using gyroscopes on both sides the accuracy of the system will increase and higher number of gait parameters will be estimated.

Finally, the feasibility of the measurement in pathologic cases, where extremely low movements or, brisk contractions of muscles can affect the quality of the signals has been shown. One major feature of the proposed method is that we have nearly the same accuracy for all three groups (coxarthrosis, prosthetic hip and control).

5 CONCLUSION

The proposed method appears a promising monitoring tool for several purposes. First, it allows measurements of gait features during a long period of walking and thus supplies the stride-to-stride variability of gait as illustrated in FIG. 10. In addition, because of its portability, this system can be used in other settings than a gait laboratory and therefore provides information that is more likely to reflect the actual performance of the subjects.

It can be used in many clinical applications such as outcome evaluation after knee and hip replacement, or external prosthesis adjustment for amputees. In elderly subjects, this system can also be proposed as a diagnostic tool for abnormal gait analysis, as a predictor tool for fall risk estimation (Najafi et al., 2001$^b$), or as a monitoring tool to assess progress through rehabilitation. During this study the system proved to have a high acceptability by elderly subjects.

REFERENCES

Figure 1:
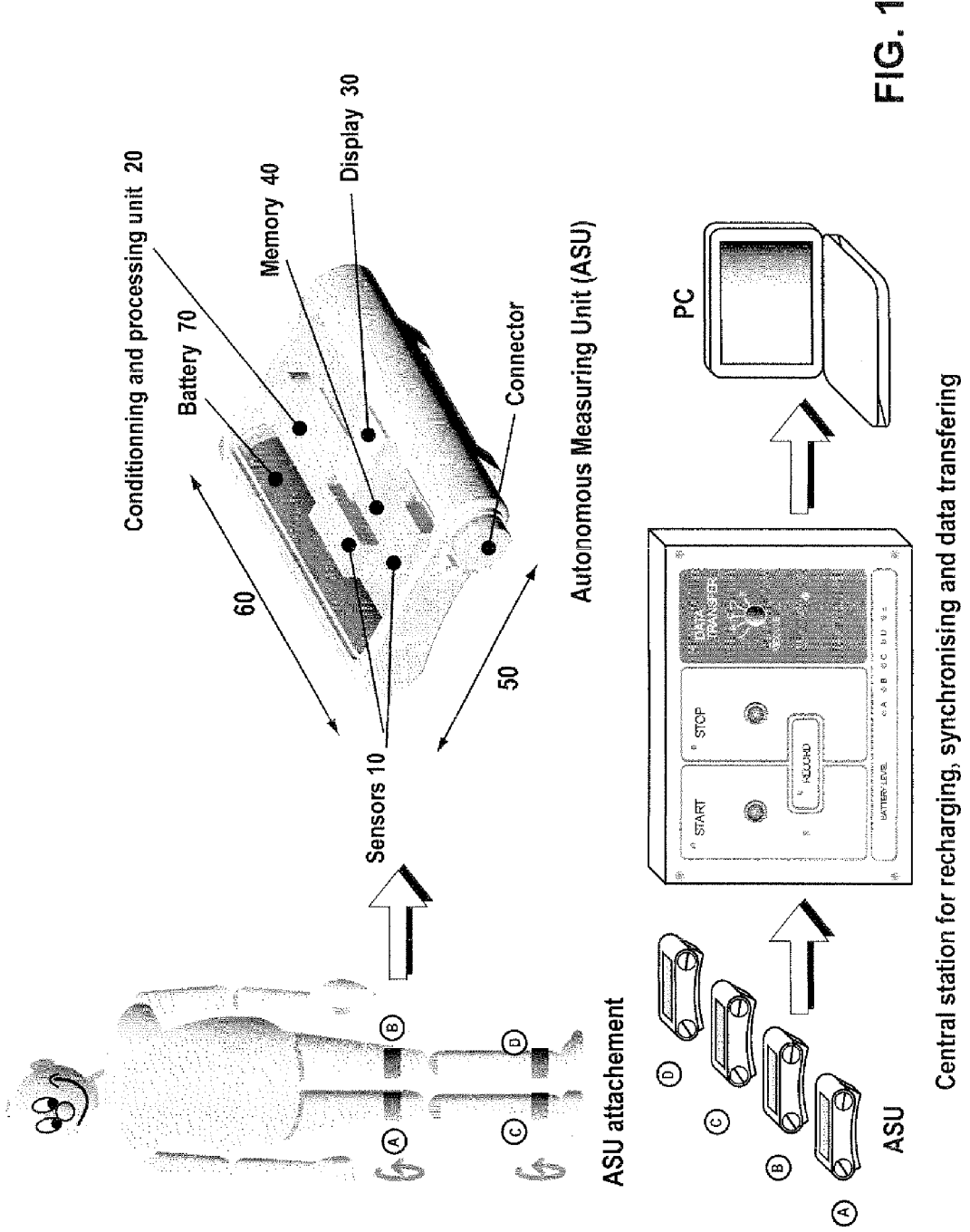
FIG. 1 Autonomous Sensing Unit (ASU) with their electronic and sensors. ASU includes one or several gyroscopes allowing the angular rate measurement of body segment. Before starting measurement all ASUs are linked to a station for synchronization. Afterward, they are disconnected from the station and record segment's movement. At the end of measurement all ASU are again connected to the station. The recorded data are transferred to the PC via station. The station allows also recharging the battery of each ASU.
Figure 2:
FIG. 2 Footswitches (FSR) attachment beneath the heel (two sensors) and beneath the big toe (two sensors).
Figure 3:
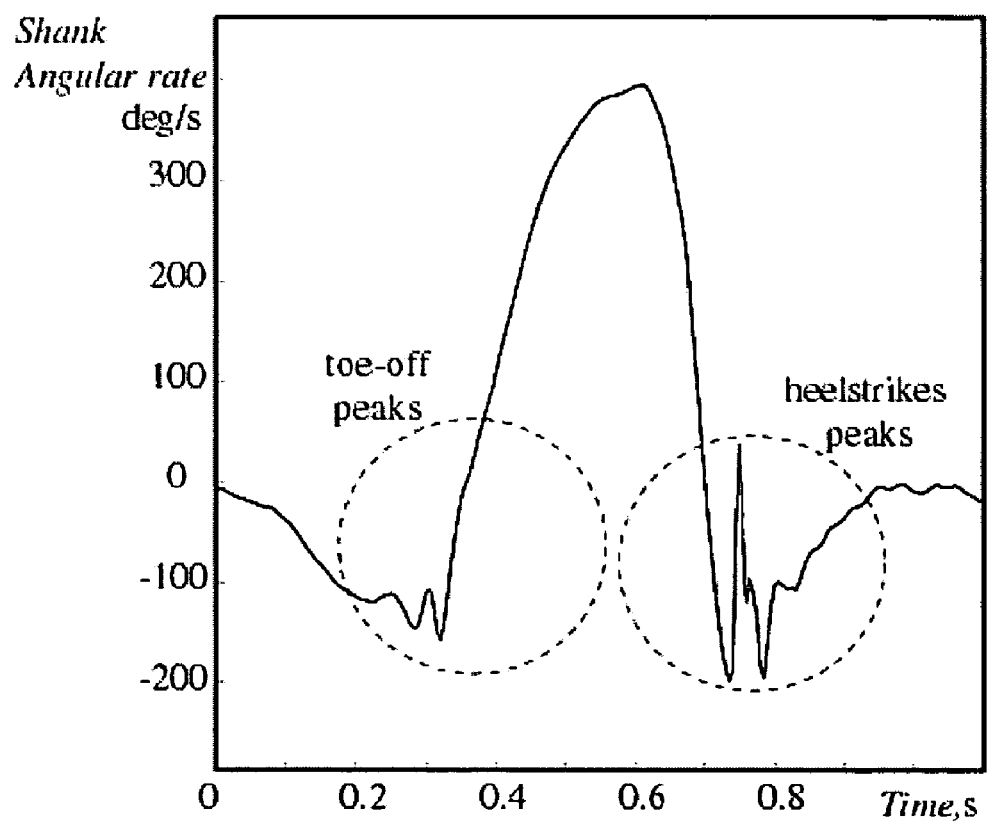
FIG. 3 Shank angular velocity showing the presence of peaks during the toe-off and heelstrike.
Figure 4:
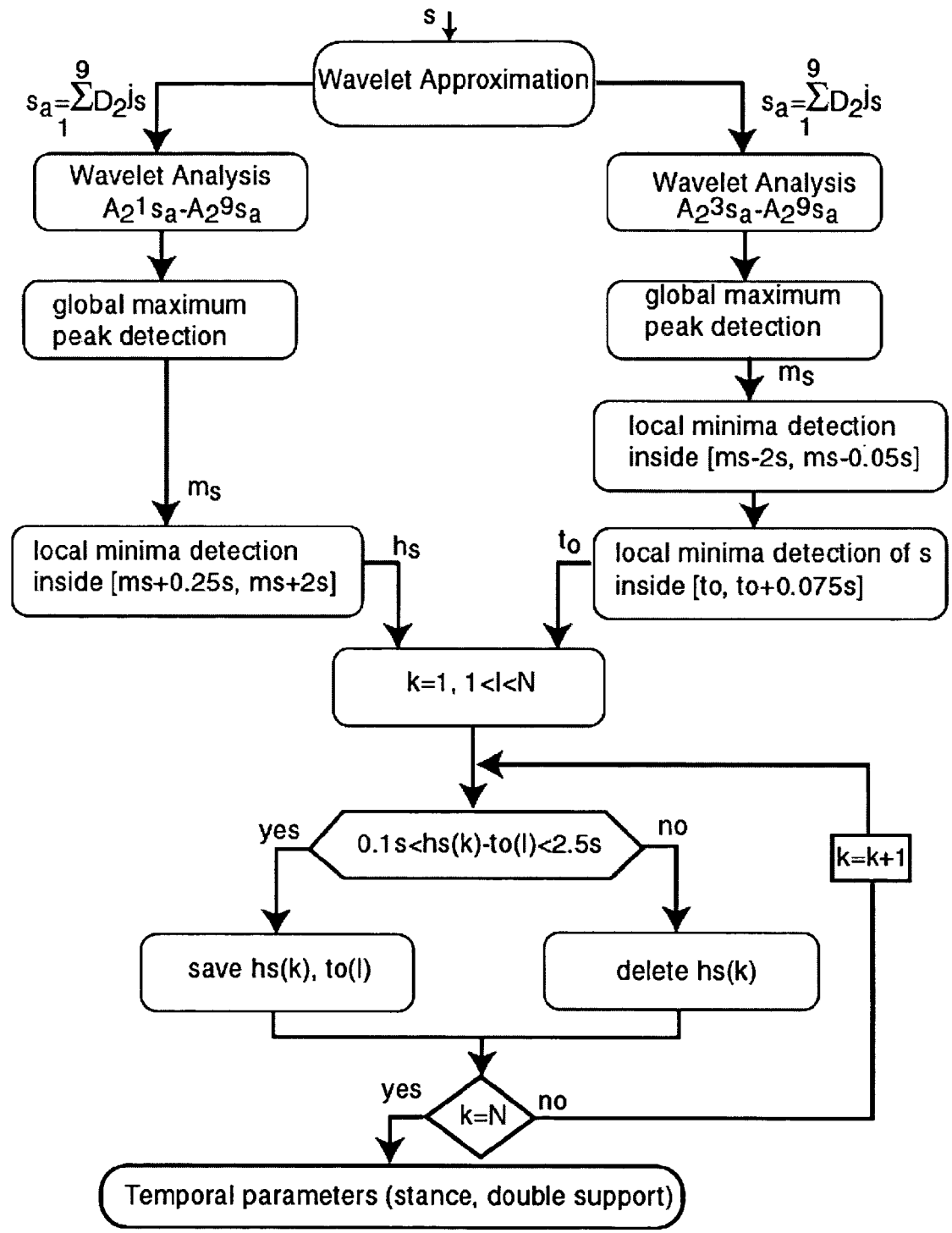
FIG. 4 Algorithm flowchart for temporal parameters estimation from shank angular rate signal (s).
Figure 5:
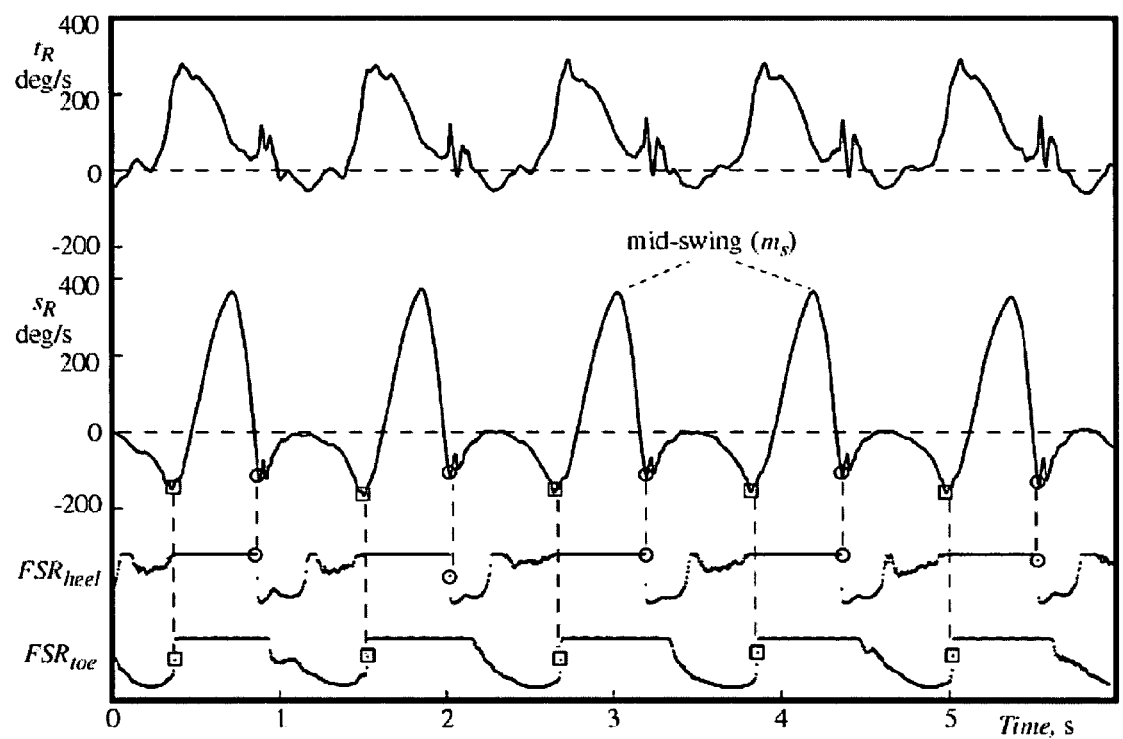
FIG. 5 FSR signal from heel ($FSR_{heel}$) and toe ($FSR_{toe}$), angular rate signal at right shank ($s_R$) and right thigh ($t_R$). Heelstrike (○) and toe-off (□) detected by FSR and $s_R$ are shown on each signal during 5 typical gait cycles. $m_s$ correspond approximately to the time of mid-swing.
Figure 6:
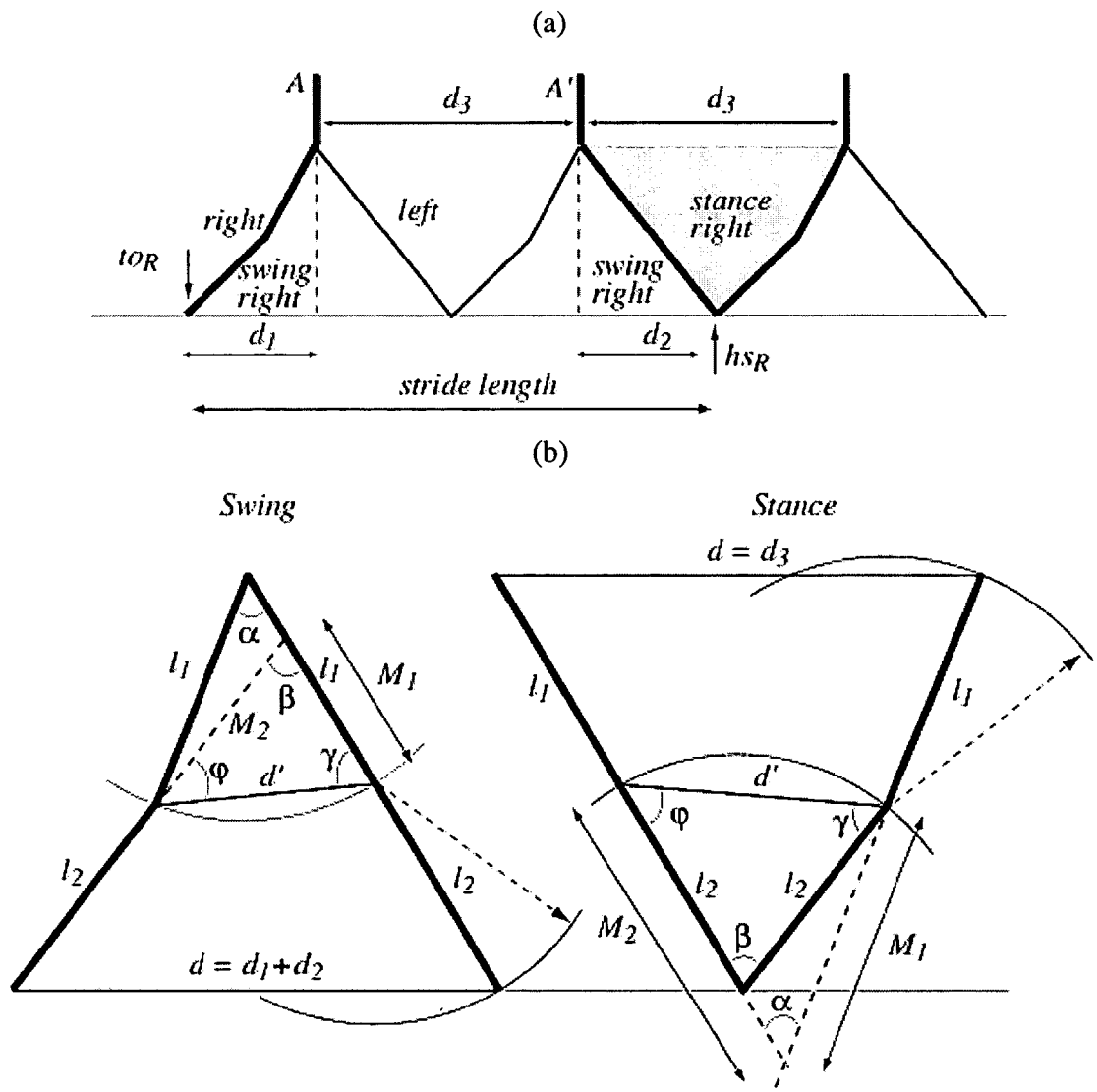
FIG. 6 (a) Body segments model during a gait cycle started by right toe-off ($to_R$) and ended by right heelstrike ($hs_R$). (b) Shank and thigh configuration during stance and swing phase. Thigh and shank length ($l_1$ and $l_2$ respectively) are measured on each subject α and β obtained from angular rate signals ($t_R$ and $s_R$) allow to estimate the distance d during stance and swing phases.
Figure 7:
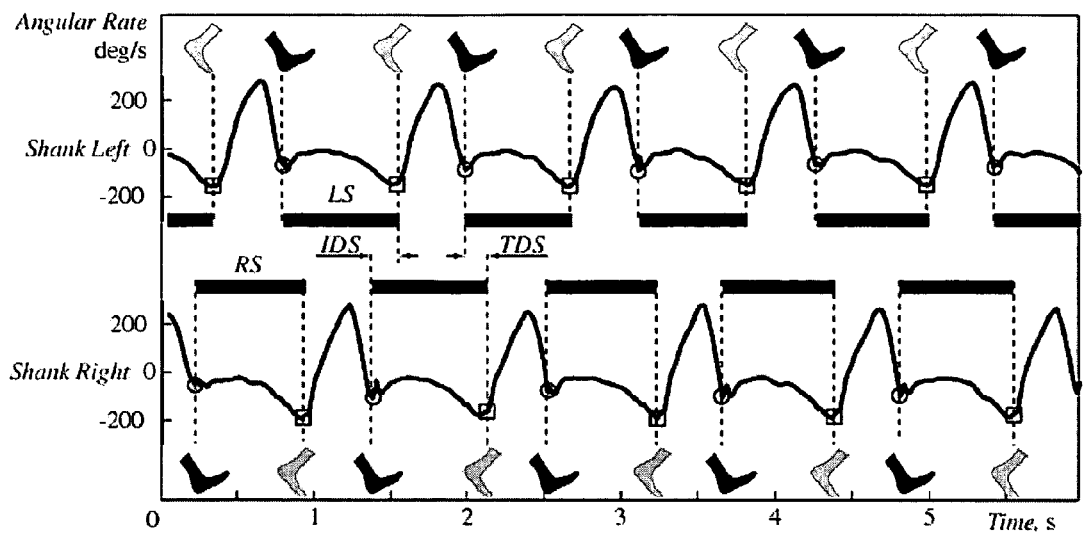
FIG. 7 Temporal parameters estimation from heelstrikes (○) and toe-offs (□) of each leg based on relation 8 to 13 in the text.
Figure 8:
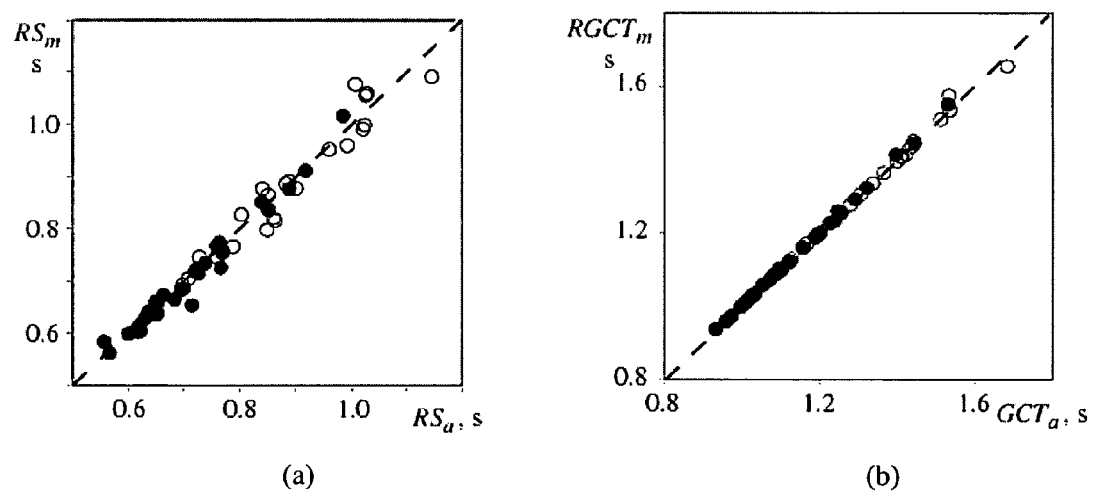
FIG. 8 (a) Right stance duration, in s, obtained from gyroscope ($RS_m$) compared with that obtained from pressure sensors ($RS_a$), r>0.99. (b) Gait cycle time from gyroscope ($RGCT_m$) compared to actual gait cycle time obtained from FRS ($GCT_a$), r>0.99. (●) young, (○) elderly subjects.
Figure 9:
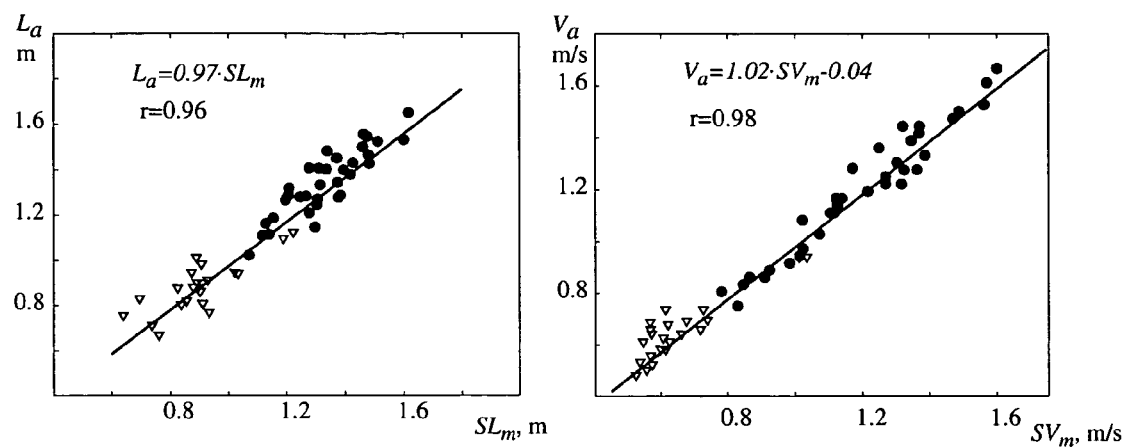
FIG. 9 Correspondence between actual stride length ($L_a$) and velocity ($V_a$) and estimated values from shank and thigh gyroscopes ($SL_m$, $SV_m$) for young (●) and elderly subjects FIG. 10. Range of thigh and shank rotation obtained from the proposed method (Measured) and Elite (Actual). Δ: group C, ○: group D, □: Group E FIG. 11 Stride velocity (SP), stride length (SL), gait cycle time(RGCT), right and left stance (RS and LS) and double support (DS) in the percent of gait cycle obtained from a young subject during 2 minutes of treadmill walking using the proposed method. The velocity of treadmill was kept at 1.11 m/s while the subject changed his cadence. All parameters are estimated at each gait cycle allowing to analyse the stride to stride variability.
Figure 10:
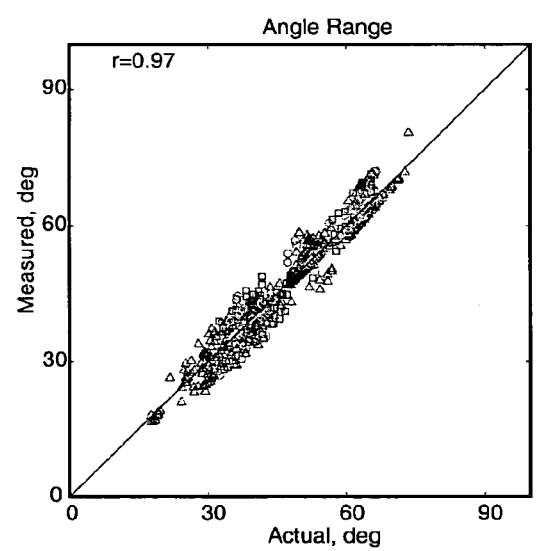
Figure 11:
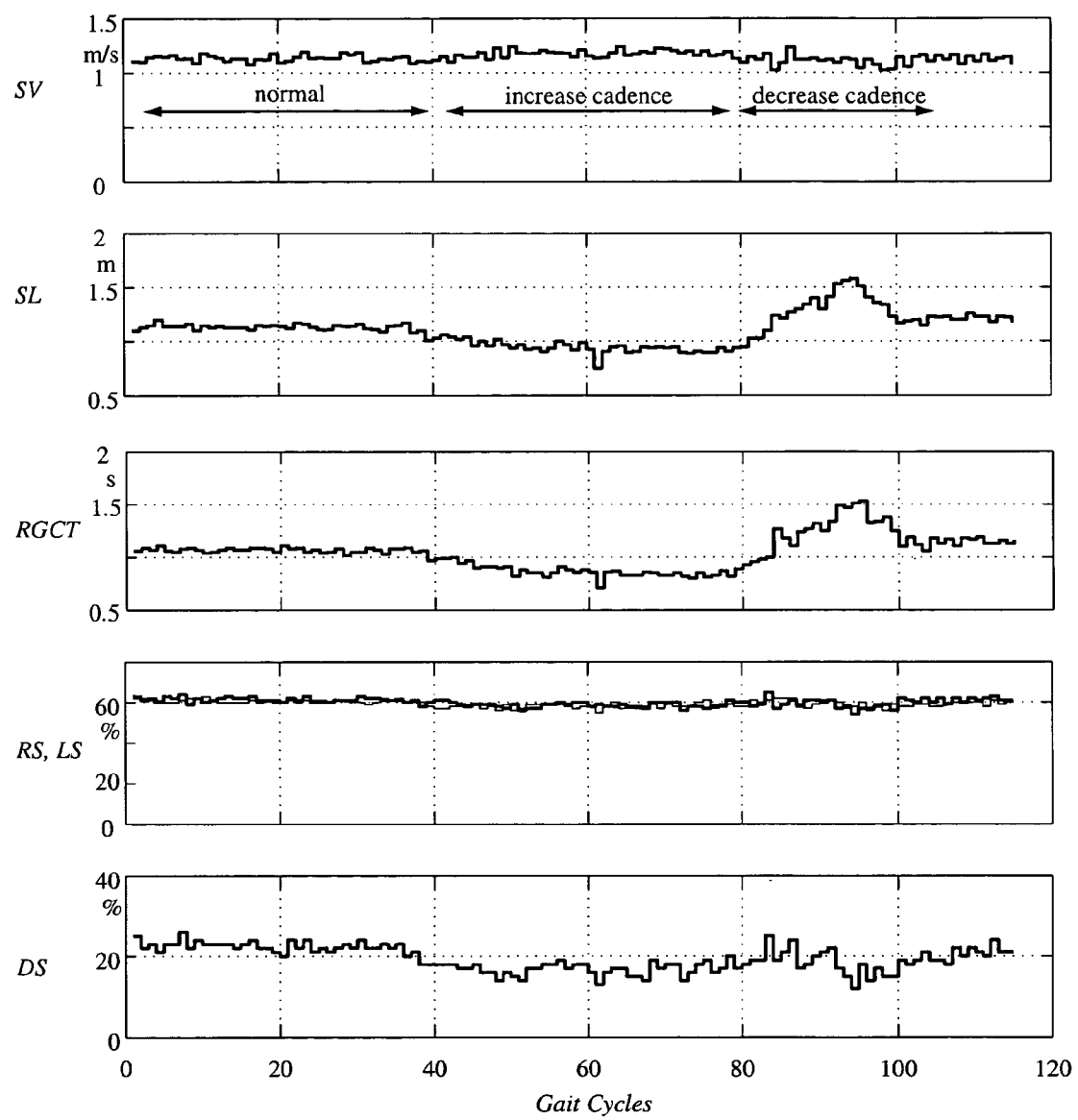

Abu-Faraj, Z O, Harris, G F, Abler, J H, Wertsch, J J, 1997. A Holter-type, microprocessor-based, rehabilitation instrument for acquisition and storage of plantar pressure data. *Journal of Rehabilitation Research and Development,* 34, 187-194.

Aminian, K, Robert, Ph, Jequier, E, Schutz, Y., 1995. Incline, speed, and distance assessment during unconstrained walking. *Medicine and Science in Sports and Exercise* 27, 226-34.

Aminian, K, Rezakhanlou, K., De Andres, E., Fritsch, C., Leyvraz, P.-F., Robert, Ph., 1999. Temporal features estimation during walking using miniature accelerometers: an analysis of gait improvement after hip arthroplasty. *Medical and Biological Engineering and Computing,* 37, 686-691.

Czemiecki, J. M, and Gitter, A. J., 1996. Gait analysis in the amputee: has it helped the amputee or contributed to the development of improved prosthetic components? *Gait and Posture,* 4, 258-268.

Evans, A L, Duncan, G, Gilchrist, W. 1991. Recording accelerations in body movements. *Medical and Biological Engineering and Computing,* 29, 102-104.

Ferrigno G., Pedotti A. ELITE: a digital dedicated hardware system for movement analysis via real time TV processing, IEEE Trans on Biomed Eng 1985; 32:943-950

Fyfe, K R, Fyfe, K W, Rooney, J K I 2000. Motion analysis system. European patent application. Bulletin 2001/2002.

Hirokawa, S., Matsumara, K., 1987. Gait Analysis using a measuring walkway for temporal and distance factors. *Medical and Biological Engineering and Computing,* 25, 577-582.

Hreljac, A, Marshall, R. N, 2000. Algorithms to determine event timing during normal walking using kinematic data. *Journal of Biomechanics,* 33.783-786.

Ismail, A R, Asfour, S S, 1999. Discrete wavelet transform: a tool in smoothing kinematic data. *Journal of Biomechanics,* 32, 317-321.

Maki, B E, 1997. Gait changes in older adults: predictors of falls or indicators of fear. *Journal of the American Geriatrics Society,* 453, 313-320.

Mallat, S G., 1989. A Theory for Multi-Resolution Signal Decomposition (The wavelet representation). *IEEE Transactions on Pattern Analysis and Machine Intelligence,* 11, 674-693.

Miyazaki, S., 1997. Long-term unrestrained measurement of stride length and walking velocity utilizing a piezoelectric gyroscope. *IEEE transactions on Biomedical Engineering,* 44, 8.

Najafi, B, Aminian, K, Paraschiv-Ionescu, A, Loew, F, Blanc, Y, Robert Ph, 2001[a], Body Postures and Walking Period Estimation Using a Kinematic Sensor: Application for Long Term Monitoring of Physical Activity in Elderly, ESMAC-2001, *Gait and Posture,* 14, 119-120.

Najafi, B, Aminian, K, Bula, C, Ruggieri, G, Robert, Ph, 2001[b], Falling Risk Evaluation in Elderly Using Miniature Gyroscope: Relation Between Gait and Risk of Falling, In: Duysens J, Stuits-Engelsman B C M and Kingma H, (Eds.), Control of posture and gait. Symposium of the International Society for Postural- and Gait research (ISPG 2001), Maastricht, pp. 135-139.

Nene, A, Mayagoitia, R, Veltink, P, 1999, Assessment of rectus femoris function during initial swing phase, *Gait and Posture,* 9, 1-9.

Pappas, I. P, Keller, Popovic, M. R, 1999. A Novel Gait Phase Detection System. In Proceeding of Automed '99, 2. Workshop, "Automatisierungstechnische Verfahren der Medizin", T U Dannstadt, pp. 69-70.

Rose, J., Gamble, J., 1994, Human walking, Baltimore. Williams & Wilkins, pp, 29, 143.

Sparks, D. R, Huang, X., Higdon, W., Johnson J. D., 1998. Angular rate sensor and accelerometer combined on the same micromachined CMOS chip. In: Microsystem Technologies 4, Springer-Verlag, pp. 139-142.

Stanhope, S. J., Kepple, T. M., McGuire, D. A., Roman, N. L., 1990. Kinematic-based technique for event time determination during gait. *Medical and Biological Engineering and Computing,* 28, 355-360.

Tong, K., Granat, M H., 1999. A practical gait analysis system using gyroscopes. *Medical Engineering and Physics,* 21, 87-94.

Vaughan, C. L., Davis, B. L., O'Coonor, J. C., 1992. Dynamics of Human Gait, Human Kinetics Publishers Champaign, Ill., pp. 33-35.

Williamson, R, Andrews, B J, 2001, Detecting absolute human knee angle and angular velocity using accelerometers and rate gyroscopes, *Medical and Biological Engineering and Computing,* 39, 294-302.

Wall, J. C., Ashburn, A., Klenerman, L., 1981. Gait Analysis in The Assessment of Functional Performance Before And After Total Hip Replacement. *Journal of Biomedical Engineering;* 3, 121-127.

Zhu, H S; Wertsch, J J; Harris, G F; Loftsgaarden, J D, Price, M B, 1991. Foot pressure distribution during walking and shuffling. *Archives of Physical Medicine and Rehabilitation,* 72, 390-397.

The invention claimed is:

1. A body monitoring system comprising:
(1) an autonomous sensing unit comprising:
  a. a set of gyroscope sensors for sensing and recording time event parameters of gait and stride velocity and stride length,
  b. a conditioning circuit for deriving information from said sensors,
  c. a display for displaying said information to an operator, and
  d. a non-transitory digital memory for recording kinematic parameters of a body segment consisting of the lower limbs of a human body, wherein the sensing unit is configured to be attached on a human's lower limbs, and wherein the lower limbs are shanks and thighs,
  and
(2) a computer configured to determine the time of initial and terminal contact (heelstrike and toe-off) of each foot, the range of rotation of each shank, each thigh and each knee, as well as the stride length and stride velocity during walking, wherein the stride length and stride velocity are determined at each cycle consisting of two steps, and wherein a double segment gait model is utilized to determine stride length based on a double pendulum during swing and an inverse double pendulum during stance, and
  wherein the computer is configured to determine the local minimum negative peaks of the shank angular velocity in order to find initial and terminal contact of the foot, and wherein the double segment gait model involving both shank and thigh is utilized in order to estimate angular rotation of lower limbs, stride length, and stride velocity.

2. A body monitoring system according to claim 1 wherein at least one of the gyroscope sensors is an angular rate sensor designed for measuring rotation of the segment on which the sensing unit is attached.

3. A body monitoring system comprising:
(1) a plurality of autonomous sensing units, and each autonomous sensing unit comprises:

a. a set of gyroscope sensors for sensing and recording time event parameters of gait and stride velocity and stride length,
b. a conditioning circuit for deriving information from said sensors,
c. a display for displaying said information to an operator, and
d. a non-transitory digital memory for recording kinematic parameters of a body segment consisting of the lower limbs of a human body, wherein the sensing unit is configured to be attached on a human's lower limbs, and wherein the lower limbs are shanks and thighs, and (2) a computer configured to determine the time of initial and terminal contact (heelstrike and toe-off) of each foot, the range of rotation of each shank, each thigh and each knee, as well as the stride length and stride velocity during walking, wherein the stride length and stride velocity are determined at each cycle consisting of two steps, and wherein a double segment gait model is utilized to determine stride length based on a double pendulum during swing and an inverse double pendulum during stance, and wherein the computer is configured to determine the local minimum negative peaks of the shank angular velocity in order to find initial and terminal contact of the foot, and wherein the double segment gait model involving both shank and thigh is utilized in order to estimate angular rotation of lower limbs, stride length, and stride velocity.

4. A body monitoring system according to claim 3 wherein at least one of the gyroscope sensors in each sensing unit is an angular rate sensor designed for measuring rotation of the segment on which the sensing unit is attached.

5. A body monitoring system according to claim 3 wherein the plurality of autonomous sensing units comprise four autonomous sensing units.

* * * * *